United States Patent [19]

De Jong et al.

[11] Patent Number: 5,332,858
[45] Date of Patent: Jul. 26, 1994

[54] ESTER COMPOSITION

[75] Inventors: Feike De Jong; Jan H. H. Meurs, both of CM Amsterdam, Netherlands

[73] Assignee: Shell Oil Company, Houston, Tex.

[21] Appl. No.: 914,395

[22] Filed: Jul. 17, 1992

[30] Foreign Application Priority Data

Jul. 22, 1991 [GB] United Kingdom ............ 9115752.9

[51] Int. Cl.$^5$ .................. C07C 67/14; C07C 69/80; C07C 69/86; C07C 57/70
[52] U.S. Cl. ..................................... 560/67; 560/86; 560/193; 562/840
[58] Field of Search .................. 560/67, 86, 100, 101, 560/102, 103, 108, 193, 109; 562/840

[56] References Cited

U.S. PATENT DOCUMENTS

| | | | |
|---|---|---|---|
| 3,462,468 | 8/1969 | Taylor et al. ................. | 560/109 X |
| 3,772,389 | 11/1973 | Lowrance ...................... | 560/86 X |
| 4,068,082 | 1/1978 | Stoffey et al. ................. | 560/86 X |
| 4,312,975 | 1/1982 | Salee et al. .................... | 560/86 X |
| 4,393,231 | 7/1983 | Misaki et al. .................. | 560/73 |
| 4,417,072 | 11/1983 | Postle et al. ................... | 560/86 |
| 4,695,649 | 9/1987 | Magami et al. ................ | 560/86 |
| 4,709,080 | 11/1987 | Spanswick et al. ............ | 560/86 |
| 4,772,743 | 9/1988 | Schmidt et al. ................ | 560/86 |
| 4,777,282 | 10/1988 | Towle ............................. | 560/86 X |
| 4,803,295 | 2/1989 | Stautgenberger et al. ..... | 560/86 X |

OTHER PUBLICATIONS

Elias et al., *Makromol. Chem.*, 182, (1981), pp. 681–686.

*Primary Examiner*—José G. Dees
*Assistant Examiner*—Vera C. Clarke

[57] ABSTRACT

The invention relates to a method for preparing an ester composition in which at least one activated phenolic ether group of a molecule is reacted with at least one haloformyl group of another molecule.

9 Claims, No Drawings

ESTER COMPOSITION

FIELD OF THE INVENTION

The invention relates to a method for preparing an ester composition, more in particular for preparing a polyester or alternatively an oligomeric ester composition.

BACKGROUND OF THE INVENTION

Polyesters are often prepared by polycondensation of hydroxyacids or dicarboxylic acids and diols, which reaction proceeds at relatively high temperatures. Suppression of side reactions as decarboxylation, dehydration of the alcohol or ether formation can be achieved by transesterification, which reaction is mainly used for the manufacturing of the important polyesters polyethyleneterephthalate (PET) and polybutyleneterephthalate (PBT). Reaction conditions usually involve prolonged heating to temperatures between 240° and 300° C. Less severe reaction conditions can be used when the carboxylic acid group is activated by using the corresponding acylchloride or mixed anhydride. Dehydrating agents as thionylchloride and phosphorous derivatives have been used to polymerize 4-hydroxybenzoic acid (cf. Polyesters 1965, Elsevier, N.Y. 1, 13 and Makromol. Chem. 1981, 182, 681).

A mild method (reaction temperature 100°-150° C.) which also enables the manufacture of compounds with both an alcohol functionality and a carboxylic acid halide in a monomer is disclosed in Makromol. Chem. Rapid Commun. 1980, 1, 457 and consists of protecting the alcohol group with trimethylsilylchloride. This method has been used for the preparation of the poly- and oligomeric ester poly(4-hydroxybenzoate) under mild conditions using 4-(trimethylsilyloxy)benzoylchloride as starting material. Poly(4-hydroxybenzoate), in particular its copolymers are valuable products in connection with their special physical properties useful as a stable engineering plastic (high crystallinity, extremely low solubility and thermotropic liquid-crystallinity) and many efforts have been made to develop a satisfactory manufacturing process with suitable monomers. This does not only apply for ester compositions based on hydroxycarboxylic acid building blocs, but also for ester compositions based on dicarboxylic acid and diol building blocs.

Most of the known ester manufacturing processes outlined above require relatively high reaction temperatures or, alternatively, they require less accessible, expensive, starting materials like silylated phenols, which materials previously need to be prepared from a phenol and trialkylchlorosilane.

Therefore there is a need for an economically attractive industrial bulk manufacturing process using cheap starting materials and operating under attractive economical, environmental and safe conditions, i.e. using rather simple equipment and resulting in a significant reduction of the cost price of the poly- and/or oligomeric ester. Consequently, considerable research and development efforts have been made for an improved manufacturing process for these ester compositions.

SUMMARY OF THE INVENTION

The present invention provides a method for preparing an ester composition by acylative ether cleavage in which at least one activated phenolic ether group of a molecule is reacted with at least one haloformyl group of another molecule. As used herein, "an activated phenolic ether group" refers to a phenolic ether derived from a phenol and a secondary-, tertiary alkyl or cycloalkylgroup, an allyl- or a benzyl group. Preferably, it is a phenolic ether derived from a phenol and a hydrocarbyl radical of the class comprising isopropyl, 2-butyl, tertiary-butyl, 2-pentyl, tertiary-pentyl, allyl, benzyl and cycloalkyl containing 5-8 carbon atoms.

DESCRIPTION OF THE PREFERRED EMBODIMENTS

It is surprising that acylative ether cleavage of activated phenolic ethers with a compound having at east one haloformyl group according to the present invention was found to be an attractive synthetic route for preparing an ester composition because norma Friedel Crafts acylation of the aromatic nucleus was to be expected on the basis of the prior art. (cf. Meerwein, H in Houben Weyl, Methoden in der organischen Chemie, fourth edition, 6/3, 155).

The phenolic ether can also be derived from a carboxylated, alkylated or arylated phenol, preferably of the class comprising hydroquinone, p,p'-bisphenol, 3- and 4-hydroxybenzoic acid, 3-propyl-4-hydroxybenzoic acid, 6-hydroxynaphthalene carboxylic acid and a dihydroxynaphthalene (more preferably from 4-hydroxybenzoic acid and 2,7- and/or 1,4-dihydroxynaphthalene).

The molecule containing at least one haloformyl group is preferably selected from the chloroformyl class of compounds comprising a benzoylchloride (unsubstituted or substituted), terephthaloyl(di)chloride, naphthalene(di)carbonylchloride and the diacylchlorides of aliphatic $C_4$-$C_9$ dicarboxylic acids.

It is recommended that the reaction conditions when preparing the ester composition are mild, e.g. the reaction can preferably be carried out at a temperature between 20° and 150° C., optionally in the presence of a catalytic amount of a Lewis acid. As used herein, "a catalytic amount" refers to an amount of from about 0.1% to 5% percent by weight of a Lewis acid. Particularly suitable Lewis acids are stannic tetrachloride, zinc dichloride and ferric chloride. Sometimes the presence of a solvent is also desirable to decrease the catalytic activity to a suitable level. Halogenated hydrocarbons e.g. chlorobenzene and tetrachloroethane are a good choice. The reaction is preferably carried out at atmospheric pressure in an inert atmosphere vis-á-vis the reactants.

In a preferred embodiment of the invention, the molecules contain on average substantially two activated phenolic ether- and/or haloformyl groups, so that the ester composition obtained is essentially unbranched.

In another preferred embodiment of the invention, each of the molecules contain one activated phenolic ether group and one chloroformyl group, so that the polyester composition obtained is homogeneous. An additional advantage of the method according to the present invention is that polyesters can be prepared from monomers that contain both (protected) phenolic hydroxy groups as well as haloformyl groups. Particularly suitable compounds containing one activated phenolic ether group are 4-isopropoxybenzoic acid and 4-benzyloxybenzoic acid. Another particularly suitable molecule which can be reacted with a dihaloformyl compound is 1,4-di-isopropoxybenzene.

Another particularly useful compound used in the practice of this invention is the ester obtainable by reacting two moles of hydroquinone ether having one activated ether group and one mole of terephthaloyl chloride. As defined above the activated ether group is derived from a hydrocarbyl group of the class comprising isopropyl, 2-butyl, tertiary-butyl, 2-pentyl, tertiary pentyl, allyl, benzyl and cycloalkyl containing 5-8 carbon atoms.

The present invention also comprises a number of novel compounds which are useful in preparing and/or in modifying ester compositions in accordance with one or more of the methods according to the present invention. These compounds are represented by the following formulas:

$RO-C_6H_4-O-CO-C_6H_4-OR$ in which R is isopropyl, 2-butyl, tertiary butyl, 2-pentyl, tertiary-pentyl, allyl, benzyl or cycloalkyl with 5 to 8 carbon atoms.

$RO-C_6H_4-O-CO-C_6H_4-CO-O-C_6H_4-OR$ in which R is isopropyl, 2-butyl, tertiary-butyl, 2-pentyl, tertiary-pentyl or allyl.

$RO-C_6H_4-CO-O-C_6H_4-O-CO-C_6H_4-OR$ in which R is isopropyl, 2-butyl, tertiary-butyl, 2-pentyl or tertiary-pentyl.

$RO-C_6H_4-O-CO-C(CH_3)_2-CH_2-CH_2-C(CH_3)_2-CO-O-C_6H_4-OR$ in which R is isopropyl, 2-butyl, tertiary-butyl, 2-pentyl, tertiary-pentyl, allyl, benzyl or cycloalkyl with 5 to 8 carbon atoms.

In the above formulas, the substituents R are preferably the same groups, but they may also be different and selected from the indicated class of groups.

In order to obtain polyester compositions with special physical properties it may be useful to adjust the average number of activated phenolic ether- and/or haloformyl groups by incorporation of a minor amount of a trifunctional compound, e.g. of the formula $ClCO-C_6H_3(-OCH(CH_3)_2)_2$, in which the isopropoxy substituents $-OCH(CH_3)_2$ are in meta positions to each other.

For the sake of completeness, it is observed that in the above formulas, $-C_6H_4-$ is meant to indicate a 1,4-phenylene group or a 1,3-phenylene group, with preference for the former.

The method according to the present invention provides inter alia valuable, novel, poly- and/or oligomeric poly(hydroxybenzoate) esters, e.g. with a degree of polymerization (dp) between 3 and 500, having in the molecules as least one end group which is an alkoxy group of the class comprising isopropoxy, 2-butoxy, tertiary-butoxy, 2-pentoxy, tertiary-pentoxy, allyloxy, benzyloxy and cycloalkoxy with 5 to 8 carbon atoms. The presence of these endgroups can e.g. be established by NMR-endgroup analysis as described in further detail below.

The polyester materials according to the present invention are inter alia useful as engineering plastics.

EXAMPLE 1

4-Isopropoxy (4-isopropoxy benzoate) (precursor)

To a stirred solution of 4-isopropoxy phenol (40 mmol, 6.08 g), 4-isopropoxy benzoyl chloride (40 mmol, 7.94 g) in 200 ml of $CH_2Cl_2$, pyridine (80 mmol, 6.32 g) was added in 20 min (RT). The mixture was stirred for 1 hour and then extracted with 10% HCl (300ml). Evaporation of the solvent and recrystallization of the remaining solid from ethanol (200 ml) gave 8.7 g (70%) of the ester. Mp 120° C.

$^1$H-NMR (CDCl$_3$, ppm$^{J(Hz)}$): 1.346$^{6.0}$(6H); 1.38$^{6.0}$(6H); 4.51$^{6.0}$(1H); 4.66$^{6.0}$(1H), 6.91$^{9.0}$(2H); 6.94$^{8.8}$(2H); 7.93$^{9.0}$(2H); 8.12$^{8.8}$(2H).

EXAMPLE 2

Polymer from adipoly chloride and 4-isopropoxy phenyl(4-isopropoxy benzoate)

To a solution of adipoyl chloride (5 mmol, 0.902g) and 4-isopropoxy phenyl(4-isopropoxy benzoate) (5 mmol, 1.570g) in 30 ml of dried toluene, 50mg of SnCl$_4$ were added. The mixture was then stirred under nitrogen for 16 hours at 60° C. The solution was filtered, the solid dissolved in 50 ml of trifluoroacetic acid and the polymer precipitated with 100 ml of methanol. After filtration, the polymer was recrystallized from pyridine. Filtration followed by washing with methanol and drying gave 0.7 g of a pale gray polymer (41%). End group analysis (NMR in CF$_3$COOD/CDCl$_3$ (1:1 v.v.) showed cleavage of 95% of the isopropyl groups, which corresponds with a dp of 10. Differential scanning calorimetry (DSC) of the polymer (heating rate 10° C./min) showed endotherms at 170° C., 178° C. (exotherm on cooling at 152° C.) and decomposition at 290°-320° C. Optical microscopy with crossed polarizers showed an anisotropic liquid state above 180° C., and a biphasic (coexisting anisotropic and isotropic phases) region between 240° C. and 310° C.

EXAMPLE 3

Diester from hydroquinone di-isopropyl ether and acetyl chloride

To a stirred mixture of hydroquinone (1 mol, 110 g), KOH (1.1 mol, 61 g) in 500 ml of methanol, isopropylbromide (1 mol, 123 g) was added in 2 hours (RT, under N$_2$). The reaction mixture was then stirred at 50° C. for 72 hours. The reaction mixture was cooled to RT and 33% HCl was added (to pH=6). Then CH$_2$Cl$_2$(500 ml) was added and the mixture extracted with water (7×500 ml) to remove hydroquinone. The organic layer was then extracted with KOH (60 g in 100 ml water). The aqueous layer was extracted twice with CH$_2$Cl$_2$ (200 ml). The solvent of the combined organic layers was evaporated and the residue distilled to give 31g of hydroquinone di-isopropyl ether (boiling point (bp) 78° C./0.026 kPa), in 16%. The aqueous layer was acidified to pH=5 with 33% HCl and extracted with CH$_2$Cl$_2$ (2×200 ml). The combined organic layers were dried over MgSO$_4$ and the solvent evaporated. Distillation of the residue gave 60-85 g (40-55%) of hydroquinone mono-isopropyl ether (bp 90°-100° C./0.026 kPa). $^1$NMR (CDCl$_3$, ppm$^{(JHz)}$): mono-ether: 1.30$^{6.0}$(6H); 4.39$^{6.0}$(1H); 5.4(OH); 6.70-6.83$^{AA'BB'}$ (4H); and the di-ether: 1.30$^{6.0}$(12H); 4.41$^{6.0}$(2H); 6.81(4H). Hydroquinone di-isopropyl ether (5 mmol) was stirred with acetyl chloride (10 mmol) and 0.1 mmols of SnCl$_4$ for 3 hours (RT) to give hydroquinone diacetate in a yield of more than 95% together with isopropyl chloride.

EXAMPLE 4

Diester from hydroquinone di-isopropyl ether and benzoyl chloride

Following the procedure described above, hydroquinone di-isopropyl ether (5 mmol) was stirred with benzoyl chloride (10 mmol) for 3 hours (RT) to give hydroquinone dibenzoate in a yield of above 80% together with isopropyl chloride and 4-isopropoxyphenyl acetate in about 10%.

The dibenzoate crystallized from the reaction mixture and prevented efficient stirring.

$^1$H-NMR (CDCl$_3$, ppm$^{J(Hz)}$): dibenzoate: 7.79 ppm (hydroquinone part) monobenzoate 6.92$^{9.2}$ and 7.12$^{9.2}$ ppm (hydroquinone part) (AA'BB').

EXAMPLE 5

4-Isopropoxy benzoyl chloride

To 4-isopropoxy benzoic acid (ex. Janssen, recrystallized from ethanol/water 50/50, mp.166° C.) (0.15 mol, 27 g), thionyl chloride (40 ml) was added in 1 hour. After standing overnight, the mixture was distilled and the fraction boiling from 114°–118° C./0.26 kPa collected, giving 28.8g of isopropoxy benzoyl chloride (96%).

$^1$H-NMR (CDCl$_3$,ppm$^{J(Hz)}$)1.37$^{6.0}$(6H); 4.67$^{6.0}$(1H); 6.92$^{9.0}$(2H); 8.04$^{9.0}$(2H).

Polymerization of 4-isopropoxy benzoyl chloride

A sample vial was filled with 2 g of isopropoxy benzoyl chloride and SnCl$_4$ was injected. The mixture was homogenized and then kept at the reaction temperature chosen. After the reaction 50 mg of the solidified red-brown reaction mixture was hydrolyzed in 1 ml of a mixture of CD$_3$OD/D$_2$O/NaOD (12:3:1, weight ratios) (2 hours, 60° C.) and the degree of polymerization (dp) was determined by NMR end-group analysis.

| | | |
|---|---|---|
| +10 mg SnCl$_4$/RT | dp = 1.5 (24 h) | dp = 2.7 (120 h) |
| +30 mg SnCl$_4$/RT | dp = 4.0 (24 h) | dp = 4.0 (120 h) |
| +100 mg SnCl$_4$/RT | dp = 4.9 (24 h) | dp = 6.0 (120 h) |
| +30 mg SnCl$_4$/60° C. | dp = 4.9 (24 h) | |
| +30 mg SnCl$_4$/130° C. | dp = 21 (24 h) | |

DSC of oligomers with a dp of approximately 4 showed an endotherm at 125° C. Microscopy with crossed polarizers showed above this temperature a highly mobile birefringent phase, which became partly isotropic above 160° C. Temperature of 100% isotropization varied from 170° C. for a freshly prepared sample to above 350° C. (decomposition) for samples heated for a second time, or samples with a stocktime of several weeks.

EXAMPLE 6

4-Allyloxy benzoic acid

To a stirred mixture of the sodium salt of methyl-4-hydroxy benzoate (0.1 mol, 17,4 g) in dimethylformaamide (100 ml), allyl chloride (0.12 mol, 9.1 g) was added in 20 min (RT). Then the mixture was stirred at 60° C. for 4 hours. After cooling, 200ml of ether were added and the mixture extracted with water (3×100 ml). After evaporation of the solvent, the residue was stirred in 100 ml of methanol with KOH (0.2 mol, 13 g) at 60° C. for 4 hours. Then 300 ml of water were added, the methanol evaporated and the aqueous layer extracted with 200 ml of ether. Precipitation of the acid with HCl, followed by recrystallization from ethanol/water gave 11.5 g of allyloxy benzoic acid (65%), mp 165° C.

$^1$H-NMR (CDCl$_3$/10%C$_5$D$_5$N, ppm$^{J(Hz)}$) 4.51$^m$(2H); 5.28$^m$(2H); 5.98$^m$(1H); 6.87$^{8.7}$(2H); 8.03$^{8.7}$(2H); 6–7(-1×OH).

4-Allyloxy benzoyl chloride

The procedure is the same as that described above for isopropoxy benzoylchloride (bp.108°–112° C./0.026 kPa 13.6 g, 66% yield) $^1$H-NMR (CDCl$_3$, ppm$^{J(HZ)}$) 4.62$^m$(2H); 5.36$^m$(2H); 6.04$^m$(1H); 6.97$^{9.0}$(2H); 8.06$^9$(2H).

Polymerization of 4-allyloxy benzoyl chloride

The procedure is the same as that described for isopropoxy benzoyl chloride. (2 g of the acid chloride was reacted at ambient temperature with 100 mg of SnCl$_4$ for 2 hours and gave a red-brown solid with a dp of 4.4).

EXAMPLE 7

4-Benzyloxy benzoic acid

The procedure is the same as that described for 4-allyloxy benzoic acid. Yield 14.3 g (63%), mp 192° C. 1H-NMR (CDCl$_3$, ppm$^{J(Hz)}$): 4.96(2H); 6.88$^{8.8}$ 8.00$^{8.8}$(2H).

Polymerization of 4-benzyloxy benzoyl chloride

The acid (2 g) was stirred in CHCl$_2$—CHCl$_2$ (10 ml) and thionyl chloride (2 ml) for 18 hours at ambient temperature. Then at 60° C. and reduced pressure, excess of thionyl chloride was distilled, together with ca. 5 ml of the tetrachloroethane. After cooling to ambient temperature, SnCl$_4$ (0.1 g) was added. The reaction mixture remained colourless and solidified in ca. 2 hours. After 24 hours solvent and benzyl chloride formed were evaporated (RT, 13.3 Pa) and the remaining pale grey solid analyzed as described above, which showed a dp of 7.5.

EXAMPLE 8

Di(4-isopropoxyphenyl)terephthalate

To a solution of 4.56 g (30 mmol) 4-isopropoxyphenol in 40 ml dry pyridine, was added a solution of 3.05 g (15 mmol) tetramethyladipoylchloride in 20 ml tetrachloroethane. After stirring at room temperature overnight, and another 3 hours at 60° C., methanol (250 ml) was added. The precipitate was washed with methanol, dried at 60° C. under vacuum, to give 6.4 g (quantitative yield) of crude product. mp: 192°–194° C. $^1$H-NMR (CDCl$_3$): δ8.30 (s, 4H), 7.12 (d, 4H), 6.91 (d, 4H), 4.51 (q, 2H), 1.35 (d,12H). In trifluoroacetic acid (TFA): 10.80 (d, 4H), 9.57 (d, 4H), 9.57 (s, 4H), 7.10 (q, 2H), 3.85 (d, 12H). $^{13}$C-NMR (CDCl$_3$): 166.7, 155.3, 144.5, 130.6, 130.5, 122.1, 117.8, 73.4, 21.0. IR (nujol): 1725 (C=O) cm$^{-1}$.

EXAMPLE 9

Ester from hydroquinone isopropyl n-propylether and acetyl chloride

Hydroquinone isopropyl n-propylether was reacted with acetyl chloride for 3 hours (RT) to give 4-n-propoxyphenyl acetate (yield >98%) together with isopropyl chloride.

1H-NMR (CDCl$_3$, ppm$^{J(Hz)}$ of the acetate: 1.00$^{7.5}$(3H); 1.76$^{7.5}$(2H); 2.24(3H); 3.87$^{7.5}$(2H); 6.84$^{9.2}$(2H); 6.95$^{9.2}$(2H) (AA'BB').

EXAMPLE 10

Ester from hydroquinone isopropyl n-propylether and benzoyl chloride

Hydroquinone isopropyl n-propyl ether was reacted with benzoyl-chloride for 3 hours (RT) to give 4-n-propoxyphenyl benzoate (yield more than 80%) together with isopropyl chloride.

1H-NMR (CDCl$_3$, ppm$^{j(Hz)}$) of the benzoate: 1.04$^{7.5}$(3H); 1.82$^{7.5}$(2H); 3.92$^{7.5}$(2H); 6.93$^{9.1}$(2H); 7.12$^{9.1}$(2H) (AA'BB'); Benzoate protons were hidden under excess of benzoyl chloride.

EXAMPLE 11

4-Benzyloxy-3-propyl-benzoic acid and polymerization

To a stirred solution of the sodium salt of methyl 4-hydroxy benzoate (0.5 mol, 87 g) in dimethylformamide (400 ml) allylchloride (0.55 mol, 42 g) was added in 2 hours (inert atmosphere, RT). After stirring in addition for 20 hours, diethylether (400 ml) was added and the mixture extracted with 400 ml of water, 400 ml of 5% HCl and 400 ml of water. Then the etheral solution was dried over MgSO$_4$, the solvent evaporated and the residue analyzed, showing almost pure 4-allyloxy-methyl benzoate. $^1$H NMR (CDCl$_3$, ppm$^{j.Hz}$): 3.86(3H); 4.56$^m$(2H); 5.25–5.45$^m$(2H); 6.03$^m$(1H); 6.91$^{8.8}$(2H); 7.97$^{8.8}$(2H).

The ether-ester obtained was heated to 220° C. for 4 hours giving 3-allyl-4-hydroxy benzoate (contaminated with ca. 20% of the corresponding coumaran and ca. 25% of the corresponding styrene).

$^1$H-NMR (CDCl$_3$, ppm$^{(j.Hz)}$): 3.42$^m$(2H); 3.88(3H); 5.10$^m$(2H); 6.00$^m$(1H); 6.88$^{8.4}$(1H); 7.81$^{8.4}$(1H); 7.84(1H); 5.0(—OH).

The Claisen product so obtained was stirred in ethanol (400 ml) under a hydrogen atmosphere for 18 hours using 10% Pd/C (Bg) as a catalyst. After filtration and evaporation of the solvent, the residue (88 g) consisted of 3-propyl-4hydroxy-methyl benzoate (contaminated with the coumaran, ca. 20%).

$^1$H-NMR (CDCl$_3$, ppm$^{j(Hz)}$);2 0.96$^{7.8}$(3H); 1.65$^{7.8}$(2H); 2.61$^{7.8}$(2H); 3.94(3H); 6.81$^{8.4}$(1H); 7.7–8.6(2H); 6.4(—OH) (Characteristic signals of the coumaran 1.486$^{6.4}$(3H); 2.82$^{7.5-15.4}$(1H); 3.33$^{8.0/15.4}$(1H); 5.00$^{6.4/7.5/8.0}$.

The ester was dissolved in dimethylformamide (400 ml) and potassium-t-butylate 0.5 mol, (61 g) was added in 1 hour, followed by the addition of benzylchloride (0.5 mol, 63.3 g) in 1 hour (RT). After stirring for 48 hours the mixture was worked up as described for the allyl ether, giving 122 g of 4-benzyloxy-3-propylmethyl benzoate (together with the coumaran).

$^1$H-NMR (CDCl$_3$, ppm$^{j(Hz)}$): 1.00$^{7.3}$(3H); 1.71$^{7.3}$(2H); 2.72$^{7.3}$(2H); 3.91(3H); 5.16(2H); 6.93$^{10.3}$(1H); 7.3–7.5(5H); 7.91$^m$(2H).

The benzyl ether was dissolved in a mixture of ethanol (400 ml), water (100 ml) and KOH (0.5 mol, 33 g) and stirred for 6 hours at 60° C. Then the ethanol was evaporated, water (300 ml) was added and the solution acidified with HCl (33%) to pH-4. The solid was collected and recrystallyzed from ethanol/water (50/50), methanol/toluene (30/70) and finally ethanol (100%) giving 66 g of pure 4-benzyloxy-3-propyl-benzoic acid (overall yield 49%, mp 163° C.).

$^1$H-NMR (CDCl$_3$/10% pyridine-D$_5$, ppm$^{j(Hz)}$): 0.77$^{7.3}$(3H); 1.50$^{17.3}$(2H); 2.51$^{7.3}$(2H); 4.93(2H); 6.75$^{9.0}$(1H); 7.1–7.3(5H), 7.83$^m$(2H)H; 4.6(—OH).

Polymerization

The ether acid (20 mmol, 5.4 g) was stirred in tetrachloroethane (100 ml) and SOCl$_2$ (5 ml) for 16 hours at 50° C. Then at this temperature excess of SOCl$_2$ and 50 ml of tetrachloroethane (TCE) were distilled off at diminished pressure. After the addition of SnCl$_4$ (0.4 g) the solution was stirred at 50° C. for 40 hours. Then methanol (150 ml) was added and the polymer precipitated by centrifugation. Decantation of the solvent followed by dissolving the polymer in tetrachloroethane (50 ml) and repeating the precipitation, gave, after drying, 3.3 g of polymer (approximately 94%). $^1$H-NMR showed that benzylation of had occurred to an extent of approximately 13%.

$^1$H-NMR (CDCl$_3$/TCE ppm): 1.09(3H); 1.74(2H); 2.70(2H); 3.95(0.3H); 6.8–7.4(2.9H); 8.21(2H).

Differential scanning calorimetry (DSC) at a heating rate of 10° C./min showed an endotherm at 243° C. on heating (exotherm at 181° C. on cooling) and decomposition starting above 360° C.

Microscopy (crossed polarizers) showed meltflow above 234° C. (nematic Schlieren texture) and isotropization at 390° C. (decomposition and isotropic behavior afterwards).

Gel permeation chromatography (tetrahydrofuran, polystyrene standard) showed a weight average of 150,000 and a polydispersity of 2.3.

EXAMPLE 12

Hydroquinone di(4-isopropoxy benzoate)

To a stirred mixture of 4-isopropoxy benzoyl chloride (15 mmol, 2.97 g) and hydroquinone (7.5 mmol, 0,825 g) in CH$_2$Cl$_2$ (50 ml), pyridine (2 ml) was added in 15 minutes. After stirring for 1 hour, the mixture was extracted with water, 10% HCl and water (100 ml each). Then the solvent was evaporated and the remaining solid recrystallized from ethanol/CH$_2$Cl$_2$ (70/30), giving 2.56 g of the product (yield 79%, melting point (mp) 195° C.).

$^1$H-NMR (CDCl$_3$, ppm$^{j(Hz)}$): 1.39$^{6.0}$(12H); 4.68$^{6.0}$)(2H); 6.96$^{8.8}$(4H); 7.25(4H); 8.14$^{8.8}$(4H)

EXAMPLE 13

Bis(4-isopropoxyphenyl)tetramethyladipate

To a solution of 4.56 g (30 mmol) 4-isopropoxyphenol in 20 ml dry pyridine, was added a solution of 3.59 g (15 mmol) tetramethyl adipoylchloride in 10 ml tetrachloroethane. After stirring at room temperature overnight, water (100 ml) and tetrachloroethane (50 ml) were added. The tetrachloroethane layer was washed with water, dried (MgSO$_4$), and the solvent evaporated. The crude product was recrystallized from ether to yield 71% of theory of the above named compound, mp 100° C., $^1$H-NMR (acetone): δ6.98 (d, 4H), 6.87 (d, 4H), 4.54 (q, 2H), 1.75 (s, 4H), 1.32 (s, 12H), 1.26 (d, 12H).

EXAMPLE 14

Polymerization of 2,6-napthalenedicarbonyl chloride and 2,7-dibenzyloxynaphthalene To a solution of the benzylether (5 mmol, 1.70 g) and the acid chloride (5 mmol, 1.67 g) in dry tetrachloroethane (10 ml) SnCl$_4$ (0.1 g) was added and the mixture stirred for 40 hours at 50° C. under a nitrogen atmosphere. Precipitation with methanol and subsequent drying gave 1.82 g of an amorphous light brown polymer showing $^1$H-NMR signals at 4.0, 7.2, and 7.6–8.6 ppm.

EXAMPLE 15

Polymerization and synthesis of 3-benzyloxy benzoyl acid

The reactions were carried out as described for 4-benzyloxy benzoic acid. 3-Benzyloxy benzoic acid was obtained in 66% yield (mp 135° C.).

$^1$H-NMR (CDCl$_3$/10% C$_5$D$_5$N, ppm): 4.86(2H); 6.88–7.26(8H); 7.56$^m$(1H); 4.6(OH).

The acid ether was converted into its chloride as described for 4-benzyloxybenzoic acid and the polymerization was carried out at 50° C. for 40 hours. The polymer partly separated from the tetrachlorethane solution as an amorphous darkbrown tar. Additional polymer precipitated upon the addition of methanol. After drying a brittle amorphous polymer (1.0 g) was obtained. A chloroform soluble fraction (ca. 50%) showed an $^1$H-NMR spectrum identical to the one published by Kricheldorf et al (POLYMER, 1982, 23, p.1821). Additional signals at 3.9 ppm indicated benzylation of the polymer to an extent of approximately 7%. End groups were not detected by NMR. The only solvent found that completely dissolved the polymer consisted of a mixture of quinoline and phenol (50/50 w.w.).

EXAMPLE 16

Preparation and polymerization of 3,5-diisopropoxy benzoic acid

To a homogenized mixture of 3,5-dihydroxy methylbenzoate (50 mmol, 8.4 g), potassium tert-butylate (110 mmol, 8.4 g) in dimethylformamide, isopropyl bromide (110 mmol, 13.5 g) was added at RT in 2 hours under an inert atmosphere. Then the mixture was stirred for 16 hours at 60° C., cooled to ambient temperature and diethylether (200 ml) and 5% HCl (100 ml) were added. The organic layer was separated and twice extracted with water (200 ml). After drying over MgSO$_4$, the solvent was evaporated and the residue stirred in a mixture of ethanol (100 ml), KOH (0.11 m) and water (20 ml) at 70° C. for 6 hours. Then the ethanol was evaporated, water (150 ml) was added and the solution acidified with 33% HCl to pH4. The solid was filtrated and recrystallized twice from ethanol/H$_2$O (70/30) to give 11.9 g of the ether-acid (64%, mp 114° C.).

$^1$H-NMR (CDCl$_3$/10%C$_5$D5N), ppm$^{(Hz)}$): 1.31$^{6.0}$(12H); 4.56$^{6.0}$(2H); 6.60$^{2.3}$(1H); 7.24$^{2.3}$(2H); 10.1(OH).

The acid (14 mmol, 4 g) was stirred with SOCl$_2$ (6 ml) overnight. Then the reaction mixture was distilled at reduced pressure giving 3,5-disopropoxy benzoyl chloride (1.7 g, 40%). Bp 120°–122° C./0.17kPa). $^1$H-NMR (CDCl$_3$, ppm$^{(Hz)}$): 1.33$^{6.0}$(12H); 4.56$^{6.0}$(2H); 6.69$^{2.3}$(1H); 7.17$^{2.3}$(2H).

The polymerization was carried in tetrachloroethane (10 ml) using 1 g of the ether halide and 0.1 g of SnCl$_4$ (4 hours at 70° C.).

$^1$H-NMR of the reaction mixture showed a dp>20 based on ratio of isopropoxy groups and isopropyl chloride formed. Extraction of the reaction mixture with K$_2$CO$_3$ (5%) followed by evaporation of the tetrachlorethane gave 0.75 g of an amorphous polymer (The CDCl$_3$ soluble fraction of the polymer of ca 30% showed broad NMR-signals at 1.3, 4.6 and 6.4–7.6 ppm).

EXAMPLE 17

2,7-Dibenzyloxy naphthalene

To a stirred solution of 2,7-dihydroxynaphthalene (50 mmol, 8.0 g) and benzylchloride (0.11 mol, 13.9 g) in dimethylformamide (200 ml), potassium tert-butylate (0.11 mol, 13.4 g) was added in 3 hours (under nitrogen, 30° C.). After stirring for 5 hours, CH$_2$Cl$_2$ (300 ml) was added and the mixture extracted with water (3×300 ml), dried over MgSO$_4$ and the solvent evaporated. Recrystallization of the residue from ethanol gave 5.5 g of the ether (32% yield, mp 161° C.).

$^1$H-NMR (CDCl$_3$, ppm$^{(Hz)}$): 5.18(4H); 7.12$^m$(4H); 7.32–7.54$^m$(10H); 7.70$^{8.5}$(2H).

EXAMPLE 18

Hydroquinone di(4-isopropoxy benzoate)

To a stirred mixture of 4-isopropoxy benzoyl chloride (15 mmol, 2.97 g) and hydroquinone (7.5 mmol, 0,825 g) in CH$_2$Cl$_2$ (50 ml), pyridine (2 ml) was added in 15 min. After stirring for 1 hour, the mixture was extracted with water, 10% HCl and water (100 ml each). Then the solvent was evaporated and the remaining solid recrystallized from ethanol/CH$_2$Cl$_2$ (70/30), giving 2.56 g of the product (yield 79%, mp 195° C.).

$^1$H-NMR (CDCl$_3$, ppm$^{(Hz)}$): 1.39$^{6.0}$(12H); 4.68$^{6.0}$(2H); 6.96$^{8.8}$(4H); 7.25(4H); 8.14$^{8.8}$(4H).

What is claimed is:

1. A method for preparing an ester which comprises reacting a molecule having at least one activated phenolic ether group and a least one chloroformyl group with a molecule having at least one chloroformyl group and at least one activated phenolic group.

2. The method according to claim 1, wherein the molecule containing at least one chloroformyl group and at least one activated phenolic ether group is 4-isopropoxy benzoyl chloride.

3. The method according to claim 1, wherein the reaction carried out at a temperature between about 20° C. and that 150° C., optionally the presence of a catalytic amount of a Lewis acid.

4. The method according to claim 3, wherein the reaction is carried out in the presence of a catalytic amount of stannic tetrachloride.

5. A compound of the formula RO—C$_6$H$_4$—O—CO—C$_6$H$_4$—OR in which R is isopropyl, 2-butyl, tertiary-butyl, 2-pentyl, tertiary-pentyl, allyl, benzyl or cycloalkyl with 5 to 8 carbon atoms and in which —C$_6$H$_4$— is a 1,4-phenylene group or a 1,3-phenylene group.

6. A compound of the formula RO—C$_6$H$_4$—O—CO—C$_6$H$_4$—CO—O—C$_6$H$_4$—OR in which R is isopropyl, 2-butyl, tertiary-butyl, 2-pentyl, tertiary-pentyl, or allyl and in which —C$_6$H$_4$— is a 1,4-phenylene group or a 1,3-phenylene group.

7. A compound of the formula RO—C$_6$H$_4$—CO—O—C$_6$H$_4$—O—CO—C$_6$H$_4$—OR in which R is isopropyl, 2-butyl, tertiary-butyl, 2-pentyl or tertiary-pentyl and in which —C$_6$H$_4$— is a 1,4-phenylene group or a 1,3-phenylene group.

8. A compound of the formula RO—C$_6$H$_4$—O—CO—C(CH$_3$)$_2$—CH$_2$—CH$_2$—C(CH$_3$)$_2$—CO—O—C$_6$H$_4$—OR in which R is isopropyl, 2-butyl, tertiary-butyl, 2-pentyl, tertiary-pentyl, allyl, benzyl or cycloalkyl with 5 to 8 carbon atoms and in which —C$_6$H$_4$— is a 1,4-phenylene group or a 1,3-phenylene group.

9. A compound of the formula ClCO—C$_6$H$_3$(—OCH(CH$_3$)$_2$)$_2$ in which the isopropoxy substituents —OCH(CH$_3$)$_2$ are in meta positions to each other and in which —C$_6$H$_4$— is a 1,4-phenylene group or a 1,3-phenylene group.

* * * * *